United States Patent [19]

Miles

[11] Patent Number: 4,505,270
[45] Date of Patent: Mar. 19, 1985

[54] FLUID ADMINISTRATION SPLINT

[76] Inventor: Betty J. Miles, Rte. 2, Box 477A, Elizabethtown, Ky. 42701

[21] Appl. No.: 498,075

[22] Filed: May 25, 1983

[51] Int. Cl.³ .................. A61F 5/04; A61F 13/00; A01K 29/00
[52] U.S. Cl. ..................... 128/88; 128/133; 119/96
[58] Field of Search ............. 604/263, 304, 305, 308, 604/178-180; 128/88, 133, 153, DIG. 6, 89 R; 119/96, 108, 143; 269/328

[56] References Cited

U.S. PATENT DOCUMENTS

| | | | |
|---|---|---|---|
| 158,893 | 1/1875 | Bissell | 128/88 |
| 2,693,794 | 11/1954 | Neville | 128/133 |
| 2,860,629 | 11/1958 | Bergholt | 604/308 |
| 3,189,073 | 6/1965 | Todd | 128/133 |
| 3,256,880 | 6/1966 | Caypinar | 128/133 |
| 3,528,413 | 9/1970 | Aydt | 269/328 |
| 3,568,671 | 3/1971 | Graham | 128/88 |
| 3,812,851 | 5/1974 | Rodriguez | 604/179 |
| 4,265,232 | 5/1981 | Stonich | 128/133 |
| 4,440,159 | 4/1984 | Cochran | 128/133 |

Primary Examiner—C. Fred Rosenbaum
Assistant Examiner—Gene B. Kartchner

[57] ABSTRACT

This device is a splint assembly around an animal's leg, for shielding a catheter taped to the leg; including an extendible splint member hinged to an extendible cover for accommodating a different length of leg, and a latch for securing the splint assembly to a door of a cage containing the animal receiving intra-venous fluid.

3 Claims, 5 Drawing Figures

U.S. Patent    Mar. 19, 1985    4,505,270
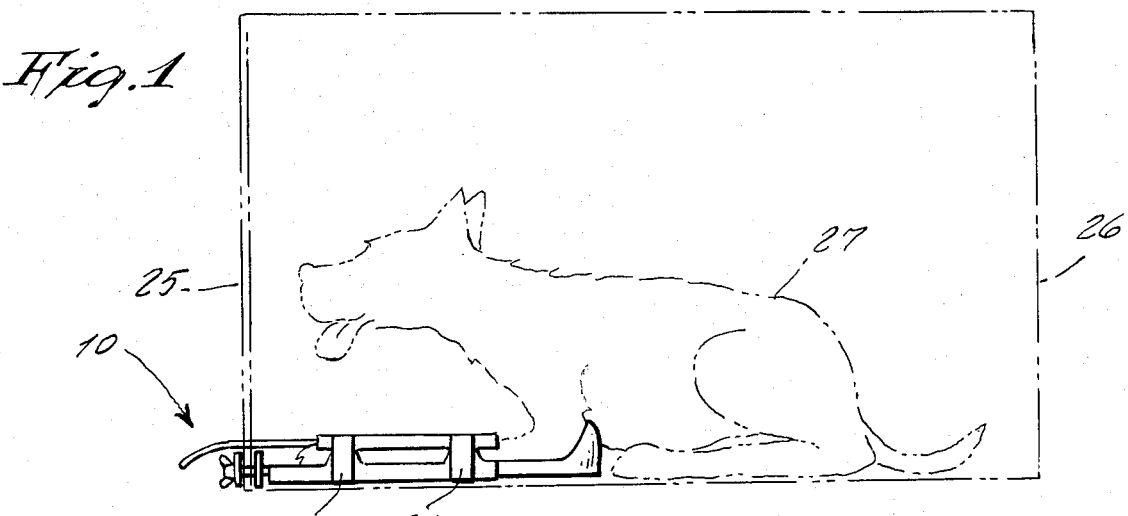
Fig.1
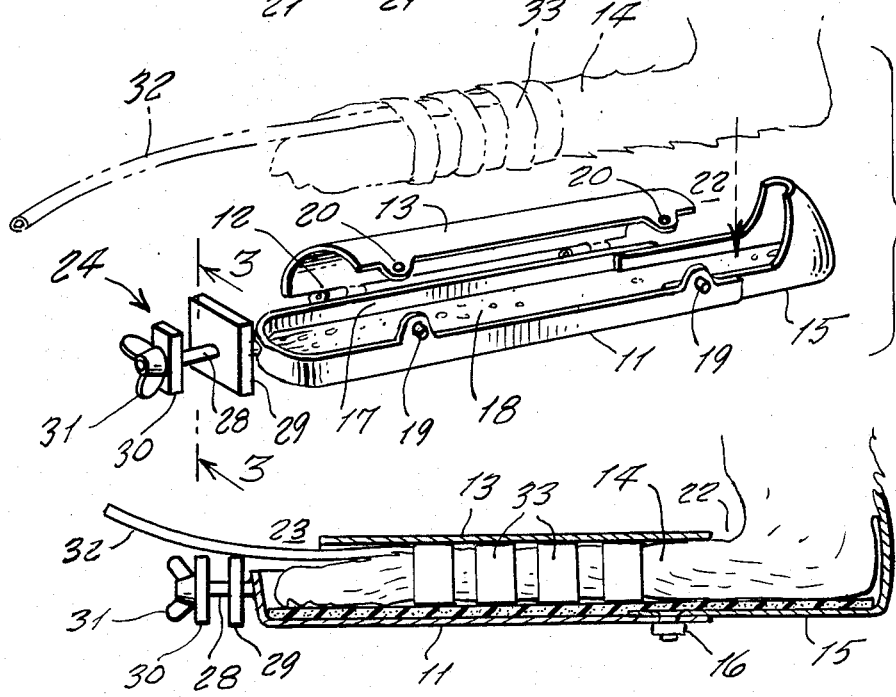
Fig.2
Fig.3
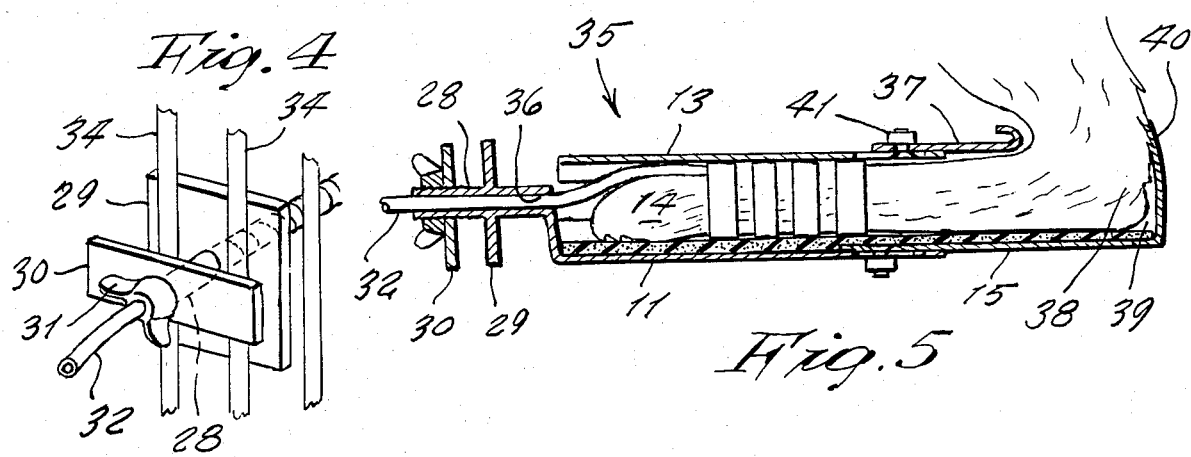
Fig.4
Fig.5

FLUID ADMINISTRATION SPLINT

This invention relates generally to animal hospital equipment. More specifically, it relates to intra-venous fluid administering equipment.

It is well known, to those persons who are experienced with the medical treatment of animals, such as cats and dogs, that unless the animal is mortally ill, the administering of intra-venous fluids is a difficult chore to accomplish. The pet chews out the intra-venous catheter or twists itself inside the animal cage, so that the intra-venous feeding tube becomes pinched off. The animal may even chew the tubing in half. This situation is objectionable, and is, therefore, in need of an improvement.

Therefore, it is a principal object of the present invention to provide a fluid administration splint, that enables intra-venous fluids to be administered to a pet, such as a cat or dog, more efficiently, so as to eliminate successfully the above indicated problems.

Another object is to provide a fluid administration splint, which keeps the pet's leg straight for administering the fluid, and wherein less tape is needed to be used to cover the catheter, because the splint covers the area that normally would have been taped.

Other objects are to provide a fluid administration splint, which is simple in design, inexpensive to manufacture, rugged in construction, easy to use, and efficient in operation.

These, and other objects, will be readily evident, upon a study of the following specification, and the accompanying drawing, wherein:

FIG. 1 is a side elevational view of the invention, shown installed on a caged dog;

FIG. 2 is a perspective view of the device, shown opened in order to receive an animal's leg that is fitted with an I.V. catheter;

FIG. 3 is a cross-sectional view, taken on line 3—3 of FIG. 2, and showing the device installed on the animal's leg;

FIG. 4 is a front perspective view of a modified design of the cage latch, through which the I.V. catheter can be inserted, for being fully enclosed in order to be protected against being bitten, and FIG. 5 is a side cross-sectional view thereof, and additionally showing a cover extension that prevents the leg from sliding forward and getting out of the splint.

Referring now to the drawing in greater detail, and more particularly to FIGS. 1 to 4 thereof, at this time, the reference numeral 10 represents a fluid administration splint, according to the present invention, wherein there is a splint member 11 attached by hinges 12 to a cover 13, so that an animal's leg 14 may be held therebetween. A slidable extension 15, in the rear end of the splint member, serves for the splint to accommodate a longer or shorter foot. The extension is locked in selected adjustment by a bolt or set screw 16. A raised peripheral lip 17 forms a central depression on the splint member and extension, that is fitted with a foam pad 18 for the animal's leg to rest thereupon. A rear end of the lip on the extension is made taller, so as to serve as an abutment for the leg joint, and prevent the leg from sliding out of the splint, when the splint is closed and locked by means of pins 19 snapping into holes 20, and a loop pile Velcro strip 21 then covering each engaged hole, and pin assembly, and extending all around the splint member and cover, as shown in FIG. 1.

The splint member, extension and cover are made from a rigid material, such as either rustproof metal or tough plastic, that cannot be chewed.

An opening 22 is formed back of a rear edge of the cover, for the animal's leg to extend therethrough. An opening 23, formed before a front edge of the cover, permits an intra-venous catheter to extend therethrough, and to the leg held in the splint.

The splint 10 includes a latch 24, for securement to a front door 25 of a cage 26, into which the treated animal 27 is placed; the latch preventing the animal from twisting around in the cage, and pinching off the catheter. The latch includes a threaded shank 28, affixed on a front end of the splint member 11, the shank having a large, square flange 29 formed around its base end. A rectangular washer 30 and a wing nut 31 is received on the shank.

In operative use of the present invention, the catheter 32 is, first, administered and secured to the animal's leg with adhesive tape strips 33. The cover is unlocked by unsnapping the pins 19 out of the holes 20, and the cover is pivoted into open position. The splint member is then placed comfortably under the leg, and the cover is snapped closed and sealed with the loop pile Velcro strips. The animal and the fluids are then prepared for transportation to the cage. The animal is placed therein, with front legs and head being toward the front of the cage. The intra-venous device is set under the cage door. The latch washer is inserted outwardly between the cage door bars 34, after which the washer is rotated ninety degrees to the position shown in FIG. 4, so that the cage door bars thus are locked between the flange and the washer. The wing nut is tightened for holding the device firmly. This allows little or no movement of the animal.

In a modified design 35 of the invention, shown in FIG. 5, and also included in the illustration of FIG. 4, the intra-venous catheter 32 is made completely inaccessible for being chewed, by inserting it through a hole 36 in the center of the shank. FIG. 5 also shows an extension 37 extendible beyond a rear edge of the cover, so as to limit forward sliding of the leg inside the splint. Thus, the rear end 38 of the leg cannot be dislodged from a pocket 39, formed by the forwardly tilted, raised lip 40 on the extension rear end. A bolt or set screw 41 locks the extension in selected position.

While various changes may be made in the detail construction, it is understood that such changes will be within the spirit and scope of the present invention, as is defined by the appended claims.

What I claim as new, is:

1. A fluid administration splint, comprising, in combination, a splint member and cover hinged together, an adjustable extension on a rear of the splint member, a raised peripheral lip around said splint member and extension forming a padded central depression for receiving an animal's leg having a catheter taped thereto, and a latch for rigidly securing said splint to a door of a cage containing an animal being treated.

2. The combination as set forth in claim 1, wherein said cover is snap-fitted in closed position on said splint member, and then secured by loop pile strips around said splint member and said cover.

3. The combination as set forth in claim 2, wherein an adjustable extension on said cover limits an access opening for said animal leg.

* * * * *